United States Patent [19]
Eggers

[11] Patent Number: 5,318,564
[45] Date of Patent: Jun. 7, 1994

[54] BIPOLAR SURGICAL SNARE AND METHODS OF USE

[75] Inventor: Philip E. Eggers, Dublin, Ohio

[73] Assignee: Hemostatic Surgery Corporation, Georgetown, Cayman Islands

[21] Appl. No.: 877,538

[22] Filed: May 1, 1992

[51] Int. Cl.⁵ .............................................. A61B 17/39
[52] U.S. Cl. ........................................ 606/47; 606/48; 606/49; 606/50
[58] Field of Search ............... 606/38, 42, 50, 51, 606/52, 47, 48, 37, 39, 40, 49, 113

[56] References Cited

U.S. PATENT DOCUMENTS

| | | |
|---|---|---|
| 3,730,188 | 5/1973 | Ellman . |
| 3,980,085 | 9/1976 | Ikuno . |
| 4,030,501 | 6/1977 | Archibald ........................... 606/37 |
| 4,041,952 | 8/1972 | Morrison, Jr. et al. . |
| 4,092,986 | 6/1978 | Schneiderman . |
| 4,196,734 | 4/1980 | Harris ................................. 606/38 |
| 4,232,676 | 11/1980 | Herczog . |
| 4,345,599 | 8/1982 | McCarrell . |
| 4,492,231 | 1/1985 | Auth . |
| 4,493,320 | 1/1985 | Treat .................................. 606/47 |
| 4,590,934 | 5/1986 | Malis et al. . |
| 4,658,819 | 4/1987 | Harris et al. ....................... 606/38 |
| 4,905,691 | 3/1990 | Rydell ................................ 606/47 |
| 4,969,885 | 11/1990 | Farin ................................. 606/38 |
| 5,026,371 | 6/1991 | Rydell et al. ..................... 606/47 |
| 5,078,716 | 1/1992 | Doll ................................. 606/47 |

Primary Examiner—Stephen C. Pellegrino
Assistant Examiner—Sonya Harris
Attorney, Agent, or Firm—Nicola A. Pisano

[57] ABSTRACT

A bipolar snare instrument for use in surgery is provided. The snare instrument has a snaring loop comprising a flexible continuous electrically-insulating loop for supporting bipolar electrodes. The electrodes may be arranged in various geometries on the insulating loop to provide localized selective necrosis and hemostasis of a patient's protruding tissue. Methods of performing surgery with such devices are also provided.

25 Claims, 8 Drawing Sheets

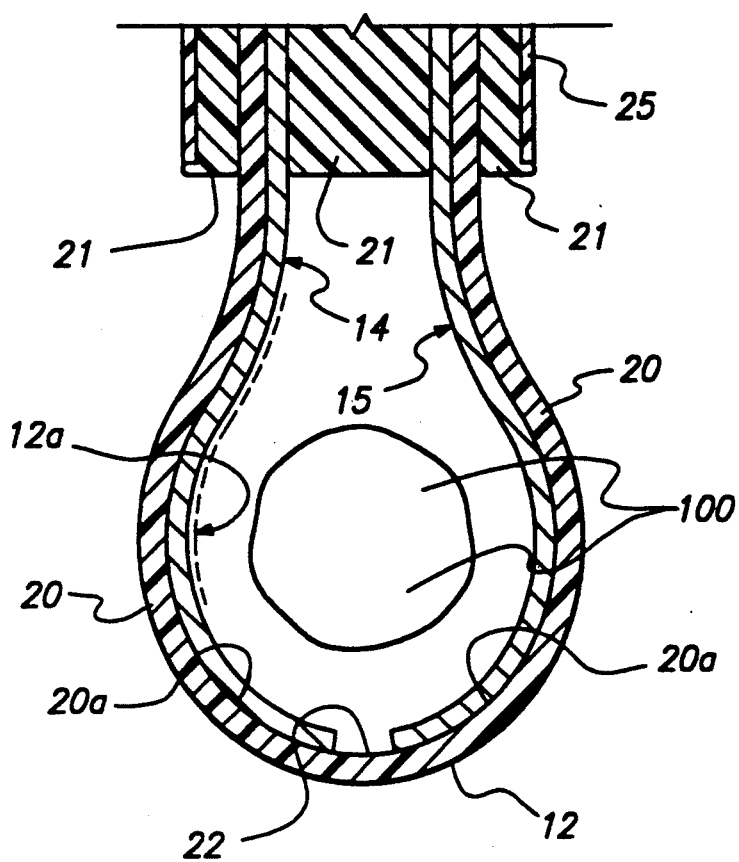
FIG. 3a
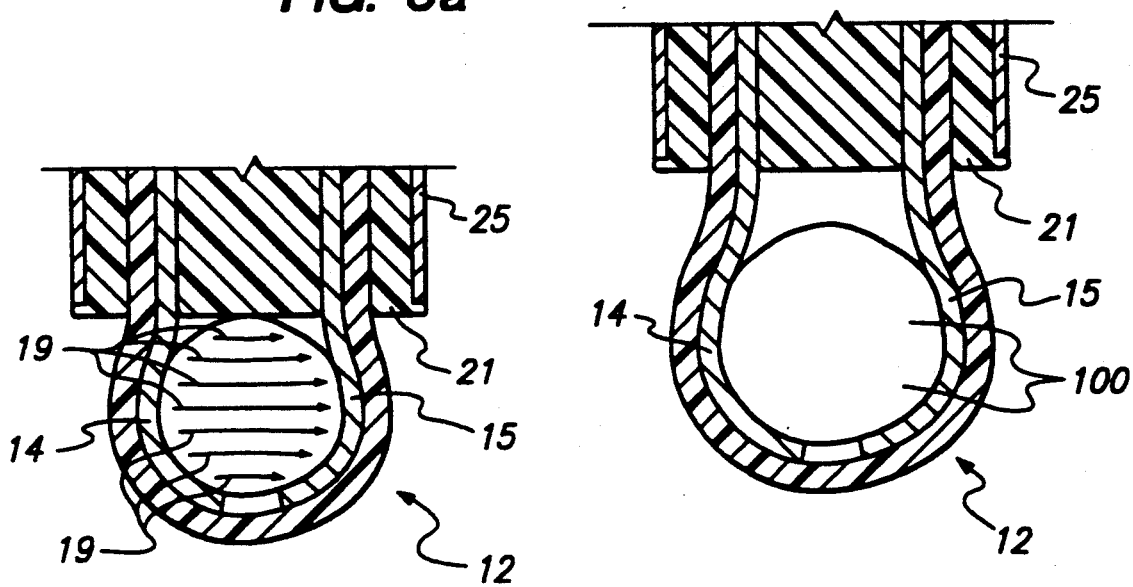
FIG. 3c
FIG. 3b

BIPOLAR SURGICAL SNARE AND METHODS OF USE

This invention relates to snares for use in surgery. More particularly, this invention relates to a bipolar surgical snare, and methods of using such snares.

BACKGROUND OF THE INVENTION

Bipolar surgical snare instruments for removing protruding tissue, such as tonsils, polyps and the like, are well known. For example, U.S. Pat. Nos. 4,493,320, 5,026,371 and 5,078,716 each describe a bipolar snare instrument that includes a pair of opposing flexible electrically conducting uninsulated snare wires connected by an electrically-insulating connector to form a snaring loop. The opposing snare wires form the bipolar electrodes of the instrument. The electrically-insulating connector isolates the opposing snare wires so that an alternating electric potential can be applied across the electrodes of the snare loop.

Each of the above-described bipolar snare instruments, suffers from one or more drawbacks associated with the use of the electrically-insulating connector to isolate the ends of the opposing Snare wires. Assembling the ends of the opposing snare wires with the electrically insulating connector adds to the complexity of the manufacturing process, since the connector must be made of an electrically-insulating material such as a plastic, ceramic, glass or epoxy-based material.

The electrically-insulating connector must form a sufficiently strong bond to the snare wires to support the loads generated during surgery. This strength requirement of the connector may also add to the complexity of the snare design. For example, Treat U.S. Pat. No. 4,493,320 describes electrically-insulating connectors having V-shaped, solid rectangular and circular-shaped forms, wherein the ends of the snare wires are imbedded in the connector.

If the bond between snare wires and the insulating connector is not capable of supporting the tensile stresses evolved during actuation of the snaring loop, the instrument may malfunction during surgery. In an extreme case, the connector may become detached from both snare wires and thus detach from the snaring instrument altogether. In endoscopic surgery, such a malfunction may have serious consequences, as it may be extremely difficult to remotely retrieve the detached connector. Additionally, should detachment of the connector go unnoticed until after surgery has been completed, the patient may require additional treatment.

A further drawback of previously known bipolar snare instruments is the need to uniformly withdraw and extend the opposing snare wires when operating the instrument. For effective selective necrosis and hemostasis of tissue, it is desirable that the lengths of the bipolar electrodes be equal throughout the range of actuation of the instrument. Some previously known bipolar snares permit the snare wires forming the electrodes to be withdrawn preferentially from side-to-side or cocked, so that the lengths of the exposed electrodes become unequal. Consequently, the selective necrosis and hemostasis achieved in such cases may be less than that desired to accomplish the objective of the surgery.

In light of the above, it would be desirable to provide an improved bipolar snare instrument for use in surgery that overcomes the drawbacks of previously known snares.

It would also be desirable to provide a snare instrument for use in surgery that does not have the design and manufacturing complexity associated with the electrically-insulating connector of previously known bipolar snare instruments.

It would further be desirable to provide a snare instrument for use in surgery that reduces the likelihood that a component of the instrument will be deposited in the internal tissue regions of a patient during surgery should a malfunction occur.

It would still further be desirable to provide a bipolar snare instrument that promotes effective selective necrosis and hemostasis of tissue by providing uniformly equal lengths of bipolar electrodes during all phases of operation, and which reduces the potential for ineffective necrosis and hemostasis caused by preferential cocking of the opposing snare wires.

SUMMARY OF THE INVENTION

In view of the foregoing, it is an object of the present invention to provide an improved bipolar snare instrument for use in surgery that overcomes the drawbacks of previously known snares.

It is another object of the present invention to provide a snare instrument for use in surgery that does not have the design and manufacturing complexity associated with the electrically-insulating connector of previously known bipolar snare instruments.

It is a further object of this invention to provide a snare instrument for use in surgery that reduces the likelihood that a component will be deposited in the internal tissue regions of a patient during surgery if a malfunction occurs.

It is a still further object of this invention to provide a bipolar snare instrument that promotes effective selective necrosis and hemostasis of tissue by providing bipolar electrodes of equal length during all phases of operation of the instrument.

In accordance with the present invention, there is provided a bipolar surgical snare instrument having a flexible snaring loop comprising a strand of continuous electrically-insulating material. First and second electrodes are disposed on the loop of electrically-insulating material to form the bipolar electrodes of the instrument.

The snare instrument further comprises a support shaft having proximal and distal ends, with the snaring loop disposed from the distal end and actuator means disposed from the proximal end for manipulating the snaring loop.

The insulating loop and first and second electrodes of the present invention may be configured so that the first and second electrodes are disposed on opposing portions of the insulating loop. In an alternative embodiment, the first and second electrodes extend continuously along upper and lower portions of the insulating loop to define an electrically-isolating gap therebetween.

In addition to providing a bipolar snare instrument, the present invention further includes methods of performing surgery on a patient's protruding tissue using an instrument having a support shaft with a distal end and a proximal end, a snaring loop with first and second electrodes disposed from the distal end of the support shaft, and actuator means disposed from the proximal end of the support shaft for manipulating the instrument and varying the circumference of the snaring loop, the methods comprising the steps of:

(a) connecting the first and second electrodes of the bipolar snare instrument to a power source for supplying AC electrical power to the instrument;

(b) creating an opening in a patient's body cavity or using a natural body orifice to provide access to the patient's tissue;

(c) inserting the working surface and support shaft of the instrument through the access opening so that the snaring loop is disposed adjacent to the patient's protruding tissue;

(d) selecting and maintaining a substantially constant voltage level output across the power source, the voltage level output independent of the impedance of the load connected across the power source;

(e) placing the snaring loop around protruding tissue;

(f) operating the actuator means to reduce the circumference of the snaring loop so that the bipolar electrodes contact the protruding tissue; and (g) activating the bipolar electrodes so that an alternating current is conducted between the electrodes and the protruding tissue to cause selective necrosis and hemostasis of the tissue.

BRIEF DESCRIPTION OF THE DRAWINGS

The above and other objects and advantages of the present invention will be apparent upon consideration of the following detailed description, taken in conjunction with accompanying drawings, in which like reference characters refer to like parts throughout, and in which:

FIG. 3A is a cross-sectional view of the snaring loop of the present invention, taken along line 3—3 of FIG. 2, showing a protruding tissue disposed within the snare;

FIGS. 3B and 3C are views, similar to FIG. 3A showing the snaring loop of FIG. 3A as it is closed upon the tissue;

DETAILED DESCRIPTION OF THE INVENTION

Figure 1:
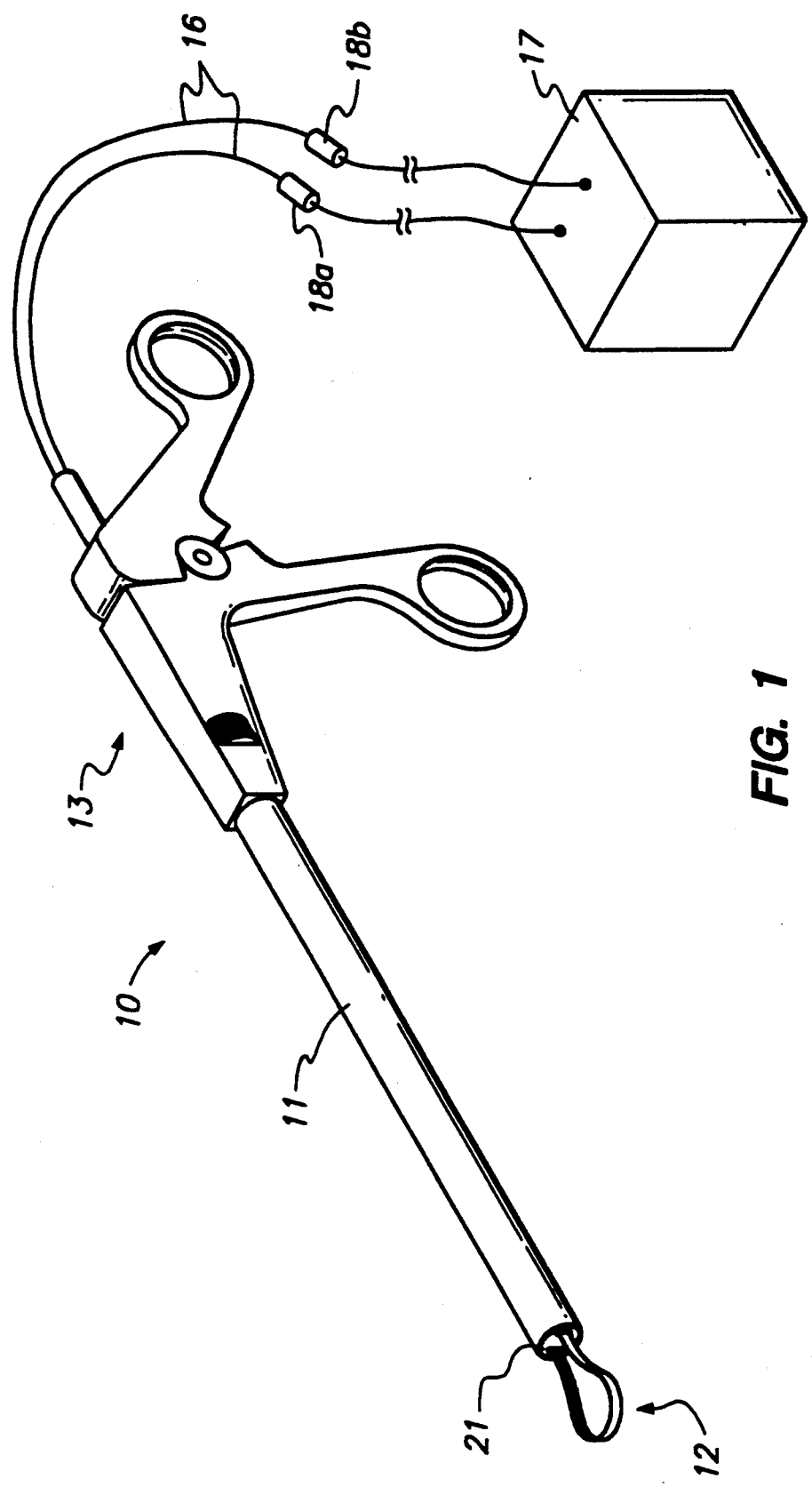
FIG. 1 is a perspective view, of bipolar surgical snare apparatus constructed in accordance with the principles of the present invention.
Figure 2:
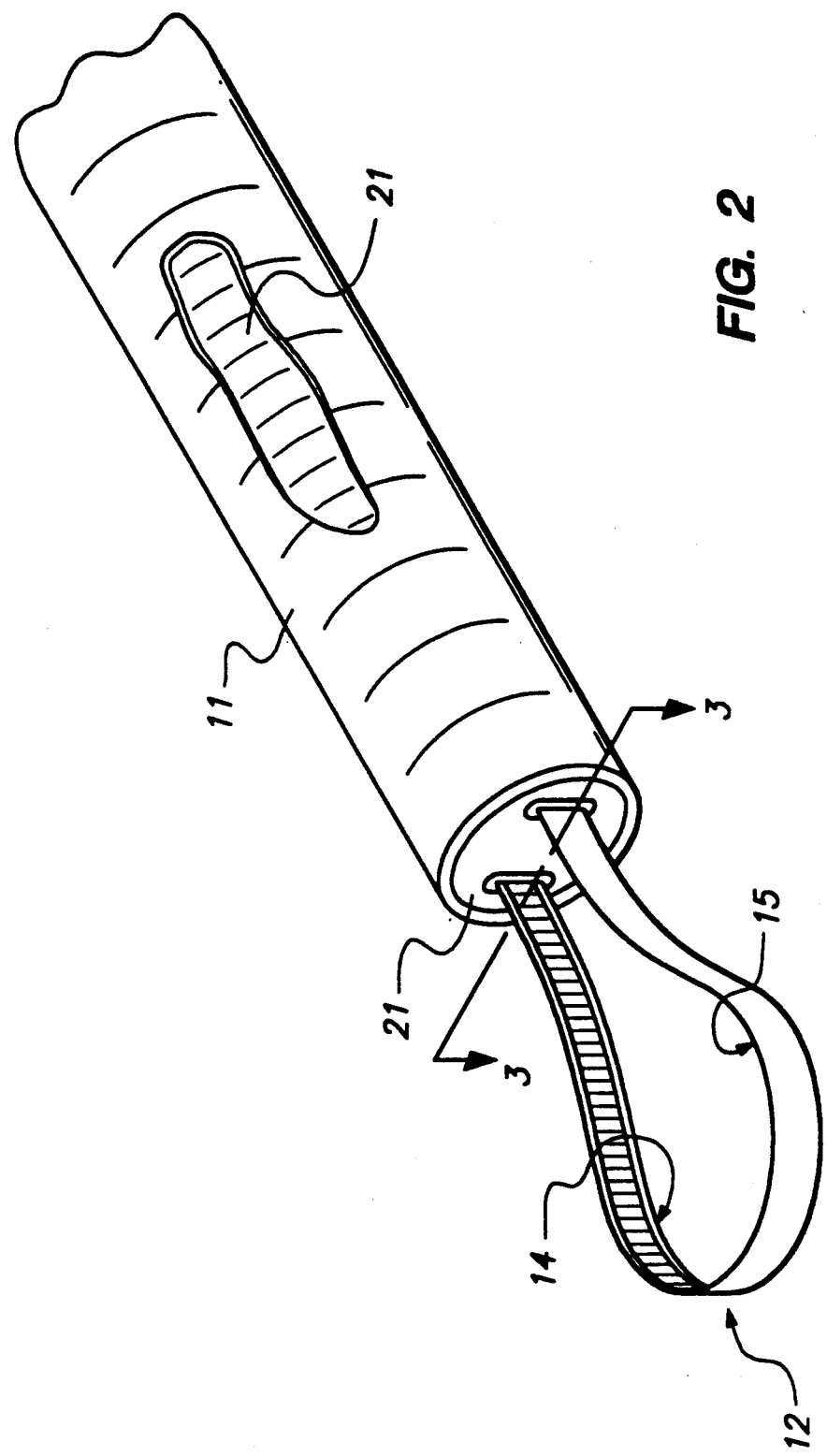
FIG. 2 is a detailed perspective view, partly in section, of the working end of the bipolar surgical snare of FIG. 1.

Referring to FIGS. 1-3, a first embodiment of snaring instrument 10 of the present invention is described. Snaring instrument 10 is used to sever protruding tissue, such as polyps or the like, and to provide localized heating to such tissues to cause selective necrosis and hemostasis. Snaring instrument 10 includes support shaft 11 having proximal and distal ends. Support shaft 11 may be either flexible or rigid, depending upon the intended application of the snaring instrument. A working end comprising snaring loop 12 projects from the distal end of support shaft 11, while snare actuator 13 for facilitating manipulation of the instrument and actuation of the snaring loop is disposed from the proximal end of support shaft 11. Snaring loop 12 includes first and second electrodes, 14 and 15, respectively, for providing bipolar cauterization. Electrical leads 16 are connected at one end to power source 17 (through electrical connectors 18a and 18b, respectively) and at the other end, through snare actuator 13, to electrodes 14 and 15, respectively.

Referring particularly to FIGS. 3A–3C, the operation of snaring instrument 10 is described. Snare actuator 13 is used to manipulate the working end of instrument 10 so that snaring loop 12 is positioned around protruding tissue 100, or other similar tissue (see FIG. 3A). The circumference 12a of snaring loop 12 may then be reduced using actuator 13 so that snaring loop 12 contacts protruding tissue 100 (see FIG. 3B). After contacting the tissue the circumference 12a of snaring loop 12 may be further contracted by actuator 13 so as to begin to sever protruding tissue 100. Alternatively, power supply 17 may be activated so as to supply an alternating-current (AC) voltage to electrodes 14 and 15 prior to further reduction in the cross-sectional area bounded by circumference 12a of snaring loop 12. A combination of these steps may also be performed, as suited for the particular surgical procedure (i.e., the snaring loop can be contracted while supplying an AC voltage; see FIG. 3C).

Power supply 17 supplies an alternating current 19 between electrodes 14 and 15 and through protruding tissue 100 (see FIG. 3C). This bipolar conduction process results in the localized heating of protruding tissue 100, in tissue regions adjacent electrodes 14 and 15. This localized heating results in elevated temperatures sufficient to cause selective necrosis and hemostasis of the tissue. The bipolar feature of snaring instrument 10 ensures that the conduction of current through tissue remote from the operative tissue is small.

In accordance with the present invention, snaring loop 12 is a composite of electrically-conducting and electrically-insulating materials. As shown in FIG. 3, snaring loop 12 is formed from a strand of electrically-insulating material having its ends connected to actuator 13 and its midsection projecting from the distal end of support shaft 11 to form a continuous loop 20. Loop 20 may be retracted or expanded by operation of actuator 13. Electrodes 14 and 15 are positioned on the inner surface 20a of electrically-insulating loop 20 to supply an AC electric potential across the tissue disposed within the loop.

Loop 20 is formed from a continuous strand of electrically-insulating flexible material suitable for carrying electrodes on its working end. In particular, the material comprising loop 20 must be capable of withstanding the tensile loads imposed by operation of the instrument. Suitable materials include, for example, KAPTON ®, a polyamide material and MYLAR ®, a polyester material, both available from E.I. du Pont de Nemours & Co., Inc., of Wilmington, Del.

In a first embodiment of the present invention, insulating loop 20 shown in FIGS. 1-3 preferably comprises a ribbon having a width of approximately 3 mm with a thickness of approximately 1 to 2 mils (25–50 microns). Of course, other geometries and dimensions are possible depending upon the particular material used and the intended application.

Insulating loop 20 extends inside support shaft 11 so that the ends of the loop are engaged with actuator 13 in the bore of support shaft 11. Intermediate connections may be disposed within the bore of support shaft 11 to facilitate connection of actuator 13 to the proximal ends of loop 12, if desired. The circumference 12a of snaring loop 12 is adjusted by reciprocating the proximal portions of loop 12 through loop holder 21. As the loop is withdrawn into support shaft 11 through loop holder 21, tissue 100 disposed within the snaring loop is first contacted and then strangulated by the loop. Selective necrosis of the tissue contacting the loop, which necrosis is caused by the current passing between electrodes 14 and 15 and the tissue, weakens the tissue and thereby permits the loop to sever the tissue.

FIG. 1 shows only one illustrative type of actuator for reducing the circumference of snaring loop 12. However, other types of actuators may be easily devised to provide the necessary action, such as pistol-and-trigger or sliding arrangements. The actuator need only provide for adjustment of the circumference, and thus cross-sectional area, of the snaring loop.

Similarly, FIG. 1 shows only one illustrative type of support shaft for carrying the snaring loop of the present invention. The carrying means should provide for manipulation and contraction of the snaring loop of the present invention as described heretofore. In a first embodiment of the present invention, support shaft 11 preferably has a diameter of approximately 5 mm so that it will fit through standard size commercially-available trocar tubes. Of course, other diameters and geometrical shapes may be desired, depending upon the intended application.

An additional feature of the present invention is that a portion of support shaft 11 near the distal end may be flexible so as to permit its insertion within a patient's curved passageway. Alternatively, the flexible portion may extend to the proximal end so that the support shaft may be inserted into a circuitous passageway, for example, an intestinal tract. Such a shaft allows snaring loop 12 to reach remote treatment sites, e.g., sites some distance beyond the entrance to the colon.

Electrodes 14 and 15 are formed on the inner surface 20a of insulating loop 20 (see FIG. 3) from an electrically-conducting material, preferably a metal or metallic alloy. Suitable materials include, for example, copper and nickel. Electrodes 14 and 15 extend into support tube 11 where they are electrically connected to electrical leads 16. Electrical leads 16 may be detachable or may be connected to electrodes 14 and 15 using conventional techniques, for example, crimping or soldering.

Electrodes 14 and 15 may be attached to the inner surface 20a insulating loop 20 using conventional techniques that provide an intimate and durable bond, such as plating, vapor deposition or chemical bonding. Electrodes 14 and 15 should adhere to insulating loop 20 with a sufficiently strong bond so that separation of the electrodes from loop 20 does not occur during surgery. This bond should also be sufficiently strong and durable to resist the deteriorating effects of multiple sterilizations. In a first embodiment of the present invention, electrodes 14 and 15 are preferably approximately 0.5 to 2 mils (12.5 to 50 microns) thick. As will be recognized by one skilled in the art, other thicknesses may be used as needed depending upon the current densities that are expected to be applied to the snaring loop.

Electrodes 14 and 15 are isolated from each other on the working end of insulating loop 20 by isolation gap 22. Isolation gap 22 reduces the likelihood of direct shorting of electrode 14 to electrode 15. Applicant has determined that for a first embodiment of the present invention isolation gap 22 should provide a gap of at least approximately 20 mils (0.5 mm) between electrodes 14 and 15.

Electrodes 14 and 15 are electrically isolated from each other within support shaft 11 by loop holder 21, which extends within the bore of support shaft 11 (see FIG. 2). Loop holder 21 is formed from an electrically-insulating material, preferably a nylon or teflon-based material, and is preferably formed by an extrusion process. Loop holder 21 extends through support tube 11 for a length sufficient to isolate electrodes 14 and 15 from each other and from support shaft 11. Of course, if snaring instrument 11 is to be inserted into an intestinal tract or other curved passageway, and support shaft 11 is thus made from a flexible material, then loop holder 21 should also be made of a flexible material to accommodate the bending of support shaft In accordance with another aspect of the present invention, if desired, electrodes 14 and 15 may also be coated with an electrically-conducting "non-stick" coating. Such a coating reduces accumulation of coagulum on the surface of loop 12. The non-stick coating should provide an intimate contact with the surface of loop 12 but not significantly impede electrical current flow through the protruding tissue. Furthermore, of course, if a non-stick coating is applied to loop 12, it should not allow electrodes 14 and 15 to electrically short together. Thus, the non-stick coating material should not be provided in regions such as isolation gap 22 or other similar regions where shorting between electrodes may occur if there is a continuous path of electrically conducting non-stick coating (e.g., the outer surface of loop 12). Masking, selective removal steps, or other conventional techniques can be used to selectively provide the non-stick coating in desired regions and thereby prevent shorting of the electrodes.

If a non-stick coating is desired, its thickness should preferably be in the range of approximately 0.5 to 1 mil (12.5 to 25 microns). Furthermore, the material may be, for example, a composite of silver and teflon. In particular, the coating may be product number RW 271790A, available from Acheson-Colloids Company, a division of Acheson Industries, Inc., Port Huron, Mich., which is a silver-filled teflon material.

In accordance with an additional aspect of the present invention, if desired, electrodes 14 and 15 may be coated with an overlayer of biocompatible metal or metallic alloy that prevents chemical interaction between electrodes 14 and 15 and tissue. Such an overlayer protects a patient from exposure to electrodes 14 and 15 should those electrodes contain constituents that might undesirably interact with a patient's tissue. Preferred overlayer materials, include, for example, platinum and titanium having a thickness of approximately 20 to 200 microns. Any conventional technique to apply the biocompatible metal overlayer to the electrodes can be used, for example, plating or vapor deposition.

Figure 4:
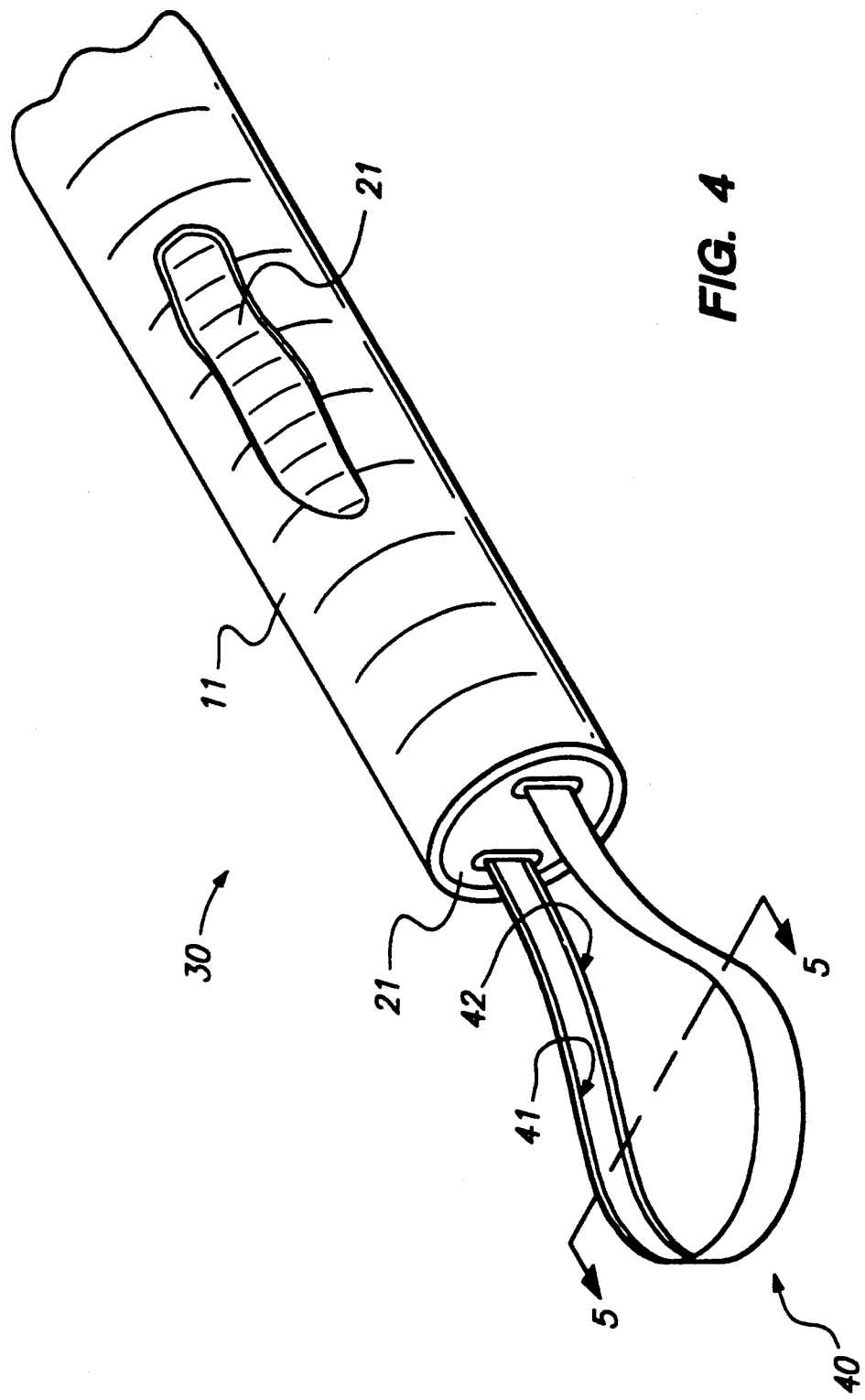
FIG. 4 is a detailed perspective view of a working end of an alternative embodiment of the snaring loop of the present invention.
Figure 5:
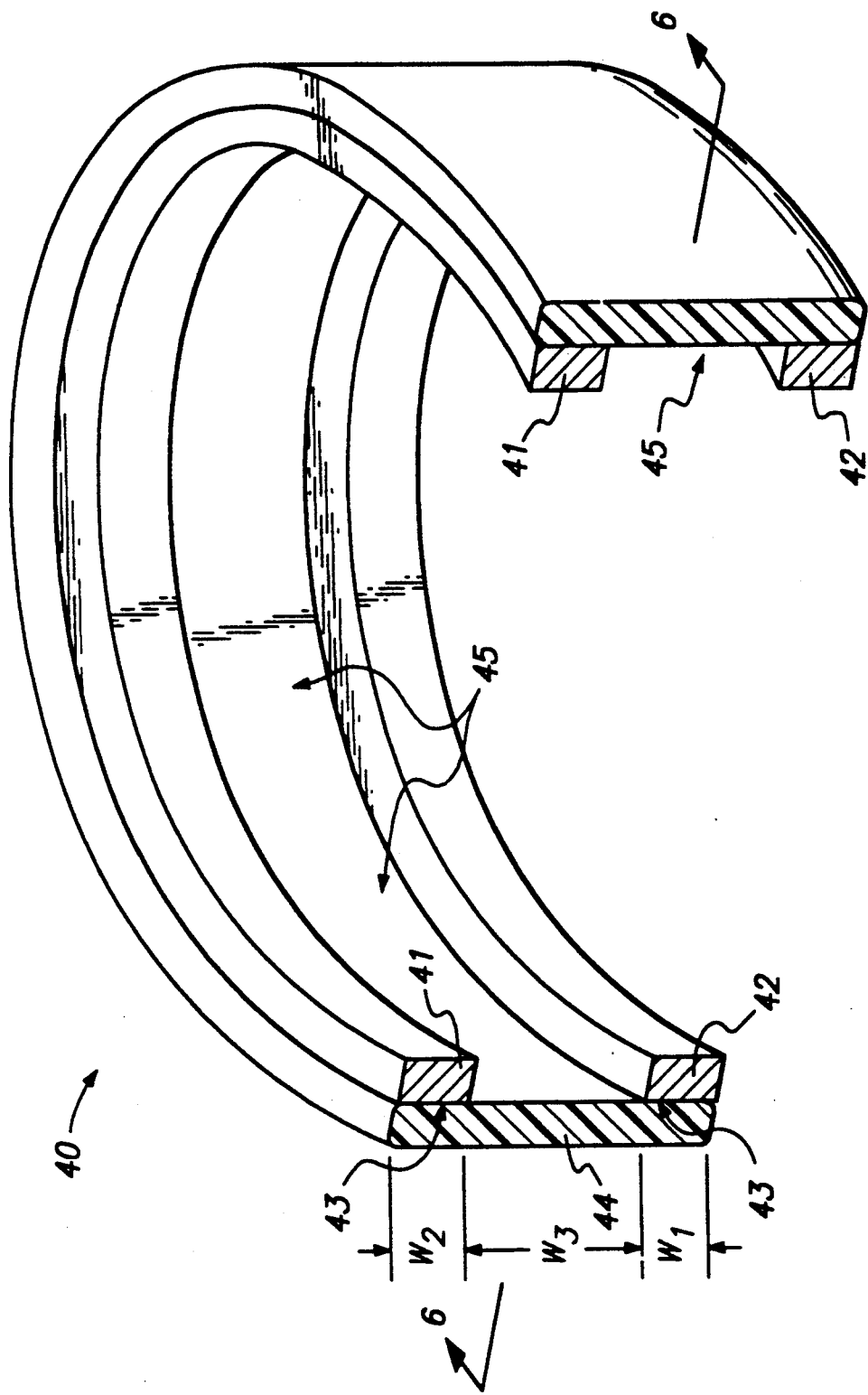
FIG. 5 is a perspective cross-sectional view of the snaring loop of FIG. 4, taken along line 5—5 of FIG. 4.
Figure 6:
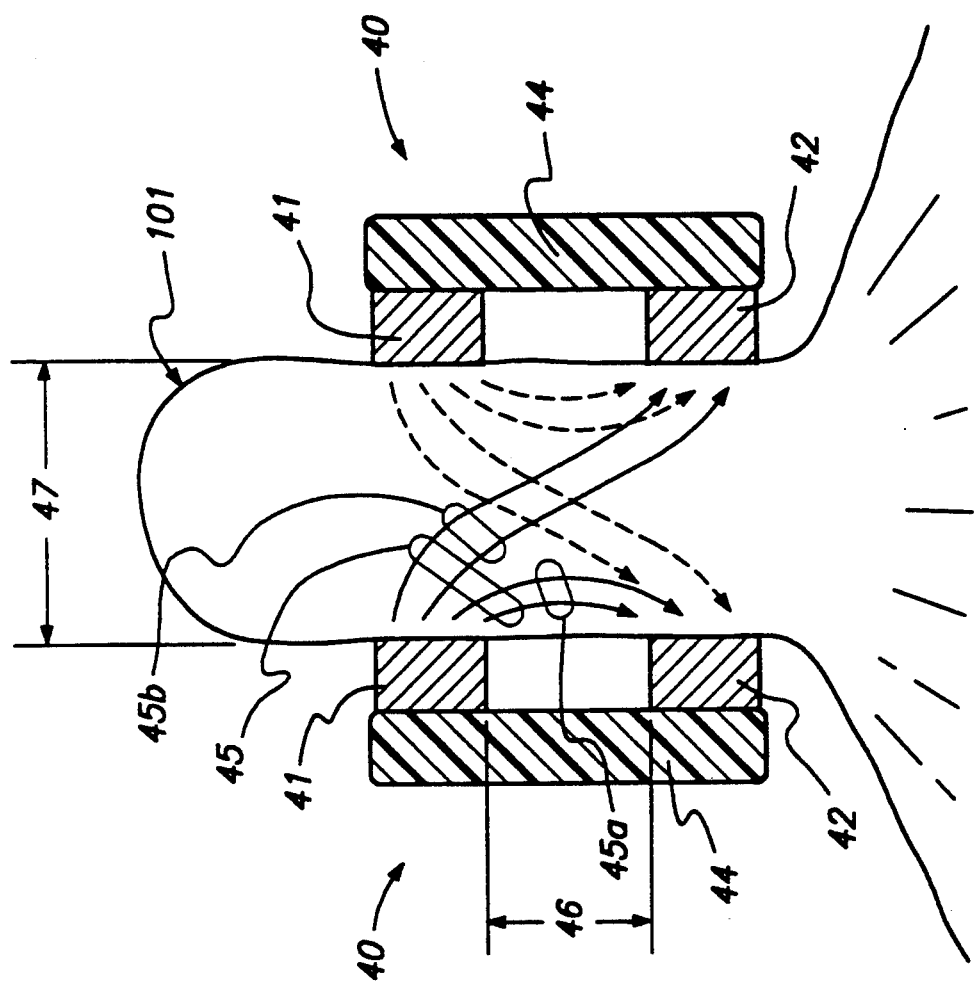
FIG. 6 is a fragmentary side view, taken along line 6—6 of FIG. 5, showing the snaring loop positioned around protruding tissue.

Referring now to FIGS. 4-6, an alternative embodiment 30 of the present invention is described. Snaring instrument 30 is similar in other respects to snaring instrument 10 shown in FIGS. 1-3, except for the structure of snaring loop 40. Thus, snaring instrument 30 includes support shaft 11, loop holder 21, an actuator (not shown) disposed from the proximal end of support shaft 11, and electrical leads (not shown) for connecting the electrodes of snaring instrument 30 to a power source.

Snaring loop 40 includes electrodes 41 and 42 disposed in parallel relation around the upper and lower portions, respectively, of the inside surface 43 of insulating loop 44. Electrodes 41 and 42 are separated by an isolation gap 45 that serves the same purpose as isolation gap 22 described with respect to the first embodiment of the present invention shown in FIGS. 1–3, i.e., it electrically isolates electrodes 41 and 42.

With particular reference to FIG. 6, snaring instrument 30 provides for selective necrosis and hemostasis of protruding tissue, such as polyps or the like, as follows. When snaring loop 40 is positioned around and contacts a protruding tissue 101, an alternating-current electrical potential is provided across electrodes 41 and 42. Alternating current 45 conducted between electrodes 41 and 42 comprises surface current 45a and bulk current 45b.

Surface current 45a conducts whenever there is a electric potential difference between electrodes 41 and 42. In accordance with the present invention, this current provides localized selective necrosis and hemostasis to tissue 101, since the distance of separation 46 between electrodes 41 and 42 is fixed by the geometry of the snaring loop. In contrast to other types of bipolar snares where each electrode forms half of the snaring loop, the current density of surface current 45a is not generally dependent upon the circumference of snaring loop 40. Thus, this embodiment provides large surface current densities to even large diameter masses of protruding tissue, because the two bipolar electrodes are maintained at a fixed distance from each other. The magnitude of this current density may therefore be fixed within a particular range by selection of the fixed separation distance 46 between electrodes 41 and 42.

A second type of current, bulk current 45b, is provided when the width 47 of protruding tissue 101 approaches the lateral separation distance 46 between electrodes 41 and 42. Bulk current 45b conducts through the bulk of protruding tissue 101, as shown in FIG. 6, when the cross-sectional area of snaring loop 40 is contracted. Advantageously, a uniform section of the protruding tissue is subjected to the current passing between the electrodes. Thus, a larger region of the tissue is weakened by the current, facilitating severing of tissue by further contraction of the snare.

The fabrication of snaring loop 40, complete with electrodes 41 and 42, is accomplished using the materials and principles discussed above with respect to the first embodiment of the snaring instrument shown in FIGS. 1–3, Preferably, the widths W1 and W2 (see FIG. 5) of electrodes 41 and 42, respectively, are approximately 1 mm. Furthermore, the separation W3 between electrodes 41 and 42, is also approximately 1 mm. Insulating loop 44 preferably has a thickness of approximately 1 to 2 mils (25 to 50 microns), and electrodes 41 and 42 preferably also have a thickness of approximately 0.5 to 2 mils (12.5 to 50 microns). Furthermore, snaring loop 40 may also contain a non-stick coating or biocompatible electrode overlayer as described heretofore with respect to snaring loop 12 of FIGS. 1–3.

Figure 7:
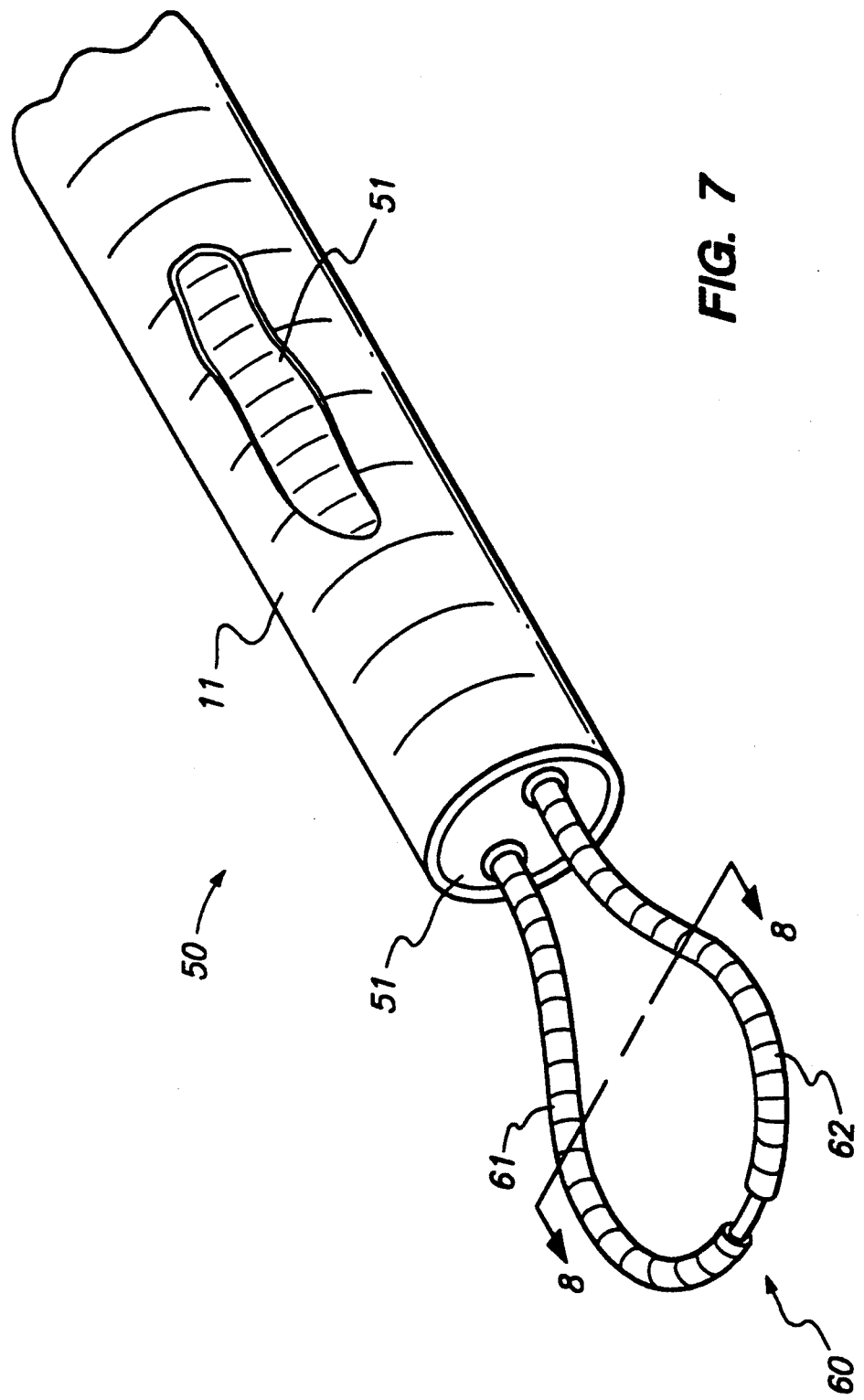
FIG. 7 is a detailed perspective view of a working end of an alternative embodiment of the snaring loop of the present invention.
Figure 8:
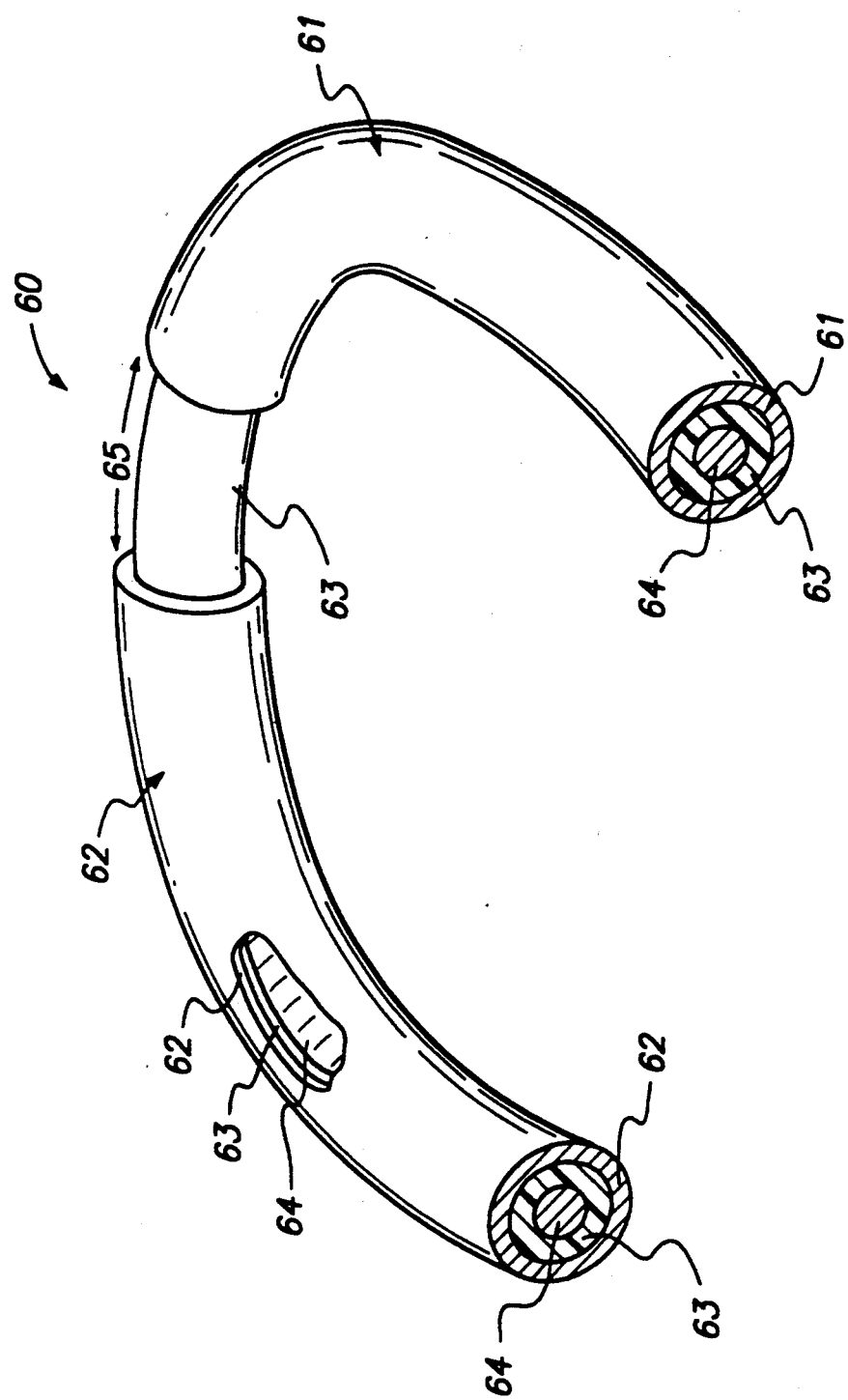
FIG. 8 is a perspective cross-sectional view of the snaring loop of FIG. 7, taken along line 8—8 of FIG. 7.

Referring now to FIGS. 7 and 8, another alternative embodiment 50 of the present invention is described. Snaring instrument 50 is similar to snaring instrument 10 shown in FIGS. 1–3, except for the structure of snaring loop 60. Thus, snaring instrument 50 includes support shaft 11, loop holder 51, an actuator (not shown) disposed from the proximal end of support shaft 11, and electrical leads (not shown) for connecting the electrodes of snaring instrument 50 to a power source.

Snaring loop 60 includes electrodes 61 and 62 disposed on a continuous insulating loop 63 of insulating material. In turn, insulating loop 63 comprises a continuous base loop 64 capable of withstanding typical tensile loads encountered by snaring loop 60. Thus, in contrast to the previously described embodiments of the present invention shown in FIGS. 1–6, the tensile loads of the snare are not imposed directly on the insulating loop of the instrument.

Base loop 64 may be a metallic wire or other similar material, preferably approximately 15 mils in diameter. Base loop 64 may be covered with an electrically-insulating material to form insulating loop 63. Preferably, insulating loop 63 comprises a 0.5 to 2 mils (12.5 to 50 microns) thick coating of, for example, a teflon-based material. The working end of snaring loop 60 is provided with an isolation gap 65 that isolates electrode 61 from electrode 62. Snaring loop 60 may also contain a non-stick coating or biocompatible electrode overlayer, as described heretofore.

The present invention also includes use of the above-described instruments in combination with a power supply that supplies an alternating-current waveform. Such devices are described, for example, in Schneiderman U.S. Pat. No. 4,092,986 and Farin U.S. Pat. No. 4,969,885.

More preferably, however, the present invention is used in combination with a power supply and control circuit that provides an AC waveform that provides a substantially constant voltage output at user-selectable levels, independent of the electrical impedance encountered by the electrodes. Preferably, the waveform allows for maximum power delivery using a minimum peak-to-peak voltage level, such as provided by the use of square waveforms. Such a power supply and control circuit is described in copending and commonly assigned U.S. patent application Ser. No. 07/871,555. This power supply and control circuit is capable of delivering an AC waveform with a selectable and substantially constant output voltage level in the form of a uniform square wave signal.

The constant output voltage-level feature of the present invention allows for the reduction in the adherence of tissue to the working surface of the snaring instrument since applicant has observed that coagulum buildup results from the use of larger peak-to-peak voltages. The use of such selectable and controllable voltages, in combination with the snaring instrument of the present invention, produces an instrument which provides substantially consistent selective necrosis and hemostasis, with little sticking or coagulum buildup.

The present invention therefore includes the method steps of employing a snaring instrument with bipolar electrodes, wherein operation of the instrument causes selective necrosis and hemostasis of protruding tissue, with little sticking or coagulum buildup on the snaring loop. As discussed above, the instrument preferably is used in conjunction with an alternating current power source having load-independent substantially constant output voltage levels. Frequencies in the range of approximately 100 kHz to 1 MHz and peak-to-peak voltages in the range of approximately 10 to 120 volts (RMS) at the electrodes of the snaring instrument, with crest factors (i.e., ratio of peak voltage to RMS voltage)

as close to unity as possible (e.g., square waveforms), are desirable.

The methods of the present invention, suitable for use in performing a great variety of surgical procedures on various types of protruding tissue using an instrument having a support shaft with a distal end and a proximal end, a snaring loop with first and second electrodes disposed from the distal end of the support shaft, and an actuator means disposed from the proximal end of the support shaft for manipulating the instrument and for expanding and contracting the snaring loop, comprise the steps of:

(a) connecting the first and second electrodes of the bipolar snare instrument to a power source for supplying AC electrical power to the instrument;

(b) creating an opening in a patient's body cavity or using a natural body orifice to provide access to the patient's tissue;

(c) inserting the working surface and support shaft of the instrument through the access opening so that the snaring loop is disposed adjacent to the patient's protruding tissue;

(d) selecting and maintaining a substantially constant voltage level output across the power source, the voltage level output independent of the impedance of the load connected across the power source;

(e) placing the snaring loop around protruding tissue;

(f) operating the actuator means to reduce the cross-sectional area of the snaring loop so that the bipolar electrodes contact the protruding tissue; and (g) activating the bipolar electrodes so that an alternating current is conducted between the electrodes and through the protruding tissue to cause selective necrosis and hemostasis of the tissue.

Operation of the apparatus in the range of 30 to 90 volts (RMS) is desirable in many cases, depending upon the impedance of the protruding tissue encountered during the surgical procedure. Of course, one skilled in the art will also recognize that the above-stated voltages are those imposed across the electrodes of the bipolar instrument, rather than the output terminals of the power source, since allowance must be made for line losses encountered in the cables connecting the snaring instrument to the power source.

The use of a power source having a selectable substantially constant voltage level output that is independent of load impedance provides sufficient power to cause selective necrosis and hemostasis of tissue. Use of a substantially constant output level reduces the power delivered to the electrodes when they are not in contact with tissue, i.e., open-circuited, and reduces the likelihood of generating a current arc when the electrodes are brought into contact with the tissue. Furthermore, use of a constant voltage level output that is independent of the load impedance inhibits excessive current flow through the tissue being operated upon. Consequently, the depth of tissue necrosis can be more precisely controlled, and localized overheating of the electrodes can be avoided. Reduced localized heating of the electrodes inhibits coagulum buildup, which interferes with both efficient coagulation and the snaring action of the instrument.

The various embodiments described herein are presented for purposes of illustration and not limitation, as the present invention can be practiced with bipolar snaring instruments of any type having two electrodes disposed on a snaring loop. The instruments and methods of the present invention may be adapted, as may be required, for use in operating on any protruding tissue, vessel, or organ.

One skilled in the art will appreciate that the present invention can be practiced by other than the described embodiments, which are presented for purposes of illustration and not of limitation, and the present invention is limited only by the claims that follow.

I claim:

1. A snare instrument for use in performing electrosurgery on protruding tissue, the instrument comprising:

a support shaft having a proximal end, a distal end, and a bore;

a strand of flexible electrically insulating material having first and second ends, the first and second ends of the strand engaged in the bore of the support shaft so that the strand forms a continuous snaring loop projecting from the distal end of the support shaft;

first and second electrodes disposed on the strand;

first and second electrical leads disposed from the proximal end of the support shaft, the first and second electrical leads connected to the first and second electrodes, respectively; and actuator means connected to the first and second ends of the strand for expanding and contracting the continuous snaring loop, the actuator means disposed from the proximal end of the support shaft, so that when the snaring loop is contracted around the protruding tissue, current may be selectively passed between the first and second electrodes to cause selective necrosis and hemostasis of the protruding tissue.

2. A snare instrument as defined in claim 1 wherein the first and second electrodes are spaced apart on the strand of flexible electrically insulating material to define an isolation gap therebetween.

3. A snare instrument as defined in claim 2 wherein the first electrode disposed on the strand extends from the first end of the strand to the isolation gap and the second electrode disposed on the strand extends from the second end of the strand to the isolation gap.

4. A snare instrument as defined in claim 2 wherein the first and second electrodes and the isolation gap extend continuously from the first end to the second end of the strand, the isolation gap electrically isolating the electrodes from each other.

5. A snare instrument as defined in claim 3 wherein the strand further comprises an inner surface, and the first and second electrodes are disposed on the inner surface.

6. A snare instrument as defined in claim 4 wherein the strand further comprises a ribbon-like configuration having an inner surface, and the first and second electrodes are disposed on the inner surface.

7. A snare instrument as defined in claim 3 wherein the strand further comprises a substantially circular cross-section having an exterior surface, and the first and second electrodes comprise metallic coatings disposed on the exterior surface.

8. A snare instrument as defined in claim wherein the strand of flexible electrically insulating material further comprises an inner strand of a high strength material having an exterior surface and a coating of electrically insulating material disposed on the exterior surface.

9. A snare instrument as defined in claim 7 wherein the strand of flexible electrically insulating material further comprises an inner strand of a high strength material having an exterior surface and a coating of electrically insulating material disposed on the exterior surface.

10. A snare instrument as defined in claim wherein the support shaft further comprises a flexible portion near the distal end to permit insertion of the support shaft into a curved passageway.

11. A snare instrument as defined in claim wherein the flexible portion extends to the proximal end to permit insertion of the support shaft into a patient's intestinal tract.

12. A snare instrument as defined in claim wherein the first and second electrodes further comprise a biocompatible overlayer that prevents chemical interaction between said electrodes and a patient's tissue.

13. A snare instrument as defined in claim wherein the first and second electrodes further comprise a coating of an electrically-conducting non-stick material.

14. A snare instrument as defined in claim 1 in combination with:
- a source of high frequency current having a selectable substantially constant voltage level output independent of the load impedance across the output;
- a first means for electrically connecting the first electrical lead to the output of the source; and
- a second means for electrically connecting the second electrical lead to the output of the source.

15. Apparatus as defined in claim 14 wherein the voltage level at the first and second electrodes is selectable form the range of approximately 10 to 120 volts (RMS) and the high frequency current is selectable from the range of approximately 100 kHz to 1 MHz.

16. A method of performing surgery on a patient's protruding tissue using an instrument having a support shaft with a distal end and a proximal end for use with a snaring loop having first and second electrodes, the snaring loop to be disposed from the distal end of the support shaft, and an actuator means disposed from the proximal end of the support shaft for manipulating the instrument and for expanding and contracting the snaring loop, the method comprising the steps of:
  (a) providing a snaring loop comprising a strand of flexible electrically insulating material having first and second ends, the first and second ends disposed from the distal end of the support shaft, the strand forming a continuous snaring loop between the first and second ends;
  (b) connecting the first and second electrodes of the bipolar snare instrument to a power source for supplying alternating-current electrical power to the instrument;
  (c) using an opening in a patient's body to provide access to the patient's tissue;
  (d) inserting the working surface and support shaft of the instrument through the opening so that the snaring loop is disposed adjacent to the patient's protruding tissue;
  (e) selecting and maintaining a substantially constant voltage level output across the power source, the voltage level output independent of the impedance of the load connected across the power source;
  (f) placing the snaring loop around protruding tissue;
  (g) operating the actuator means to contract the snaring loop so that the first and second electrodes contact the protruding tissue; and
  (h) activating the first and second electrodes so that an alternating current passes between the first and second electrodes and the protruding tissue to cause selective necrosis and hemostasis of the tissue.

17. The method of claim 16 further comprising the step of setting the voltage level output of the power source so that the voltage across the electrodes of the instrument is in the range of approximately 10 to 120 volts (RMS).

18. The method of claim 16 further comprising selecting an alternating current voltage waveform having a crest factor near unity.

19. The method of claim 16 further comprising the step of setting the power source to provide a current with a frequency in the range of approximately 100 kHz to 1 MHz.

20. The method of claim-16 wherein the step of using an opening in a patient's body to provide access further comprises using a patient's natural body orifice.

21. The method of claim 16 wherein the step of using an opening in a patient's body to provide access further comprises the step of creating an opening in the patient's body cavity.

22. A method of performing surgery on a patient's protruding tissue using an instrument having a support shaft with a distal end and a proximal end, for use with a snaring loop having first and second electrodes, the snaring loop to be disposed from the distal end of the support shaft, and an actuator means disposed from the proximal end of the support shaft for manipulating the instrument and for expanding and contracting the snaring loop, the method comprising the steps of:
  (a) providing the first electrode in the form of a continuous loop having first and second ends disposed from the distal end of the support shaft;
  (b) providing the second electrode in the form of a continuous loop having first and second ends disposed from the distal end of the support shaft;
  (c) connecting the first and second electrodes of the bipolar snare instrument to a power source for supplying alternating-current electrical power to the instrument;
  (d) using an opening in a patient's body to provide access to the patient's tissue;
  (e) inserting the working surface and support shaft of the instrument through the opening so that the snaring loop is disposed adjacent to the patient's protruding tissue;
  (f) selecting and maintaining a substantially constant voltage level output across the power source, the voltage level output independent of the impedance of the load connected across the power source;
  (g) placing the snaring loop around protruding tissue;
  (h) operating the actuator means to contract the snaring loop so that the first and second electrodes contact the protruding tissue; and
  (i) activating the first and second electrodes so that an alternating current passes between the first and second electrodes and the protruding tissue to cause selective necrosis and hemostasis of the tissue; and
  (j) maintaining a uniform spacing between the first and second electrodes during expansion and contraction of the snaring loop, so that the first and second electrodes do not contact each other.

23. The method of claim 22 further comprising the step of setting the voltage level output of the power source so that the voltage across the electrodes of the instrument is in the range of approximately 10 to 120 volts (RMS).

24. The method of claim 22 Further comprising selecting an alternating current voltage waveform having a crest factor near unity.

25. The method of claim 22 further comprising the step of setting the power source to provide a current with a frequency in the range of approximately 100 kHz to 1 MHz.

* * * * *

UNITED STATES PATENT AND TRADEMARK OFFICE
CERTIFICATE OF CORRECTION

PATENT NO. : 5,318,564  
DATED : June 7, 1994  
INVENTOR(S) : Philip E. Eggers

Page 1 of 2

It is certified that error appears in the above-indentified patent and that said Letters Patent is hereby corrected as shown below:

| Column | Line | |
|--------|------|---|
| 1 | 25 | change "Snare" to --snare-- |
| 6 | 20 | after "shaft", insert --11.-- |
| 8 | 41 | change "07/871,555" to --07/877,533-- |
| 10 | 61 | after "claim", insert --1-- |
| 11 | 4 | after "claim", insert --1-- |
| 11 | 8 | after "claim", insert --1-- |
| 11 | 12 | after "claim", insert --1-- |

UNITED STATES PATENT AND TRADEMARK OFFICE
CERTIFICATE OF CORRECTION

PATENT NO. : 5,318,564
DATED : June 7, 1994
INVENTOR(S) : Philip E. Eggers

It is certified that error appears in the above-indentified patent and that said Letters Patent is hereby corrected as shown below:

| Column | Line | |
|--------|------|---|
| 11 | 16 | after "claim", insert --1-- |
| 11 | 31 | change "form" to --from-- |
| 12 | 16 | change "claim-16" to --claim 16-- |

Signed and Sealed this

Thirteenth Day of August, 1996

*Attest:*

BRUCE LEHMAN

*Attesting Officer*   *Commissioner of Patents and Trademarks*